United States Patent [19]
Don Michael

[11] Patent Number: 5,095,898
[45] Date of Patent: * Mar. 17, 1992

[54] RESUSCITATION AID

[75] Inventor: T. Anothony Don Michael, Bakersfield, Calif.

[73] Assignee: Brunswick Bio-Medical Corporation, Wareham, Mass.

[*] Notice: The portion of the term of this patent subsequent to Mar. 12, 2008 has been disclaimed.

[21] Appl. No.: 653,638

[22] Filed: Feb. 12, 1991

Related U.S. Application Data

[63] Continuation-in-part of Ser. No. 419,658, Oct. 11, 1989, Pat. No. 4,998,530, which is a continuation-in-part of Ser. No. 202,101, Jun. 1, 1988, abandoned.

[51] Int. Cl.⁵ ............................................. A61M 16/00
[52] U.S. Cl. .......................... 128/203.11; 128/202.28; 128/207.16
[58] Field of Search ................... 128/207.12, 203.11, 128/202.28, 202.29, 207.16

[56] References Cited

U.S. PATENT DOCUMENTS

| | | | |
|---|---|---|---|
| 409,954 | 5/1943 | Martindale et al. | 128/146 |
| 1,142,990 | 6/1915 | Stern | 128/203.11 |
| 2,591,953 | 4/1952 | MacLean | 128/146 |
| 2,887,104 | 5/1959 | Sovinsuy et al. | 128/29 |
| 3,229,689 | 1/1966 | Christman | 128/29 |
| 3,252,457 | 5/1966 | Monaco et al. | 128/29 |
| 3,827,433 | 8/1974 | Shannon | 128/145.15 |
| 3,957,046 | 5/1976 | Harris | 128/203.11 |
| 3,974,829 | 8/1976 | Tate, Jr. | 128/203.11 |
| 4,305,387 | 12/1981 | Reist-Kundle et al. | 128/202.28 |
| 4,328,798 | 5/1982 | Isaacson | 128/202.27 |
| 4,449,526 | 5/1984 | Elam | 128/206.21 |
| 4,573,463 | 3/1986 | Hall | 128/205.24 |
| 4,579,114 | 4/1986 | Gray et al. | 128/203.11 |
| 4,697,587 | 10/1987 | Marinkovich | 128/203.11 |
| 4,819,627 | 4/1989 | Connors | 128/203.11 |
| 4,819,628 | 4/1989 | Eisenbert et al. | 128/203.11 |
| 4,858,605 | 8/1989 | Levy | 128/203.11 |
| 4,881,540 | 11/1989 | Vigilia | 128/203.11 |
| 4,941,873 | 7/1990 | Irwin | 128/203.11 |
| 4,998,530 | 3/1991 | Don Michael | 128/203.11 |

Primary Examiner—Eugene H. Eickholt
Attorney, Agent, or Firm—Spensley, Horn, Jubas & Lubitz

[57] ABSTRACT

A medical device for enabling a rescuer to administer mouth-to-mouth resuscitation to a victim while maintaining a sanitary barrier between victim and rescuer, composed of: a sheet of a flexible material forming a barrier to micro-organisms, the sheet being dimensioned to completely cover the victim's mouth and having an opening surrounded by a portion of the sheet which is shaped to allow the rescuer's lips to form an air-tight seal with the victim's lips; members secured to the sheet and located to pass around the victim's ears in order to hold the sheet in place so that the opening is located in front of the victim's mouth; a tubular member defining a confined air passage extending through the opening and having a first portion located to be inserted into the mouth of the rescuer and a second portion located to be inserted into the victim's mouth when the sheet is in place; and a one-way valve fastened to the first portion of the tubular member for permitting free passage of air only from the rescuer to the victim.

5 Claims, 3 Drawing Sheets

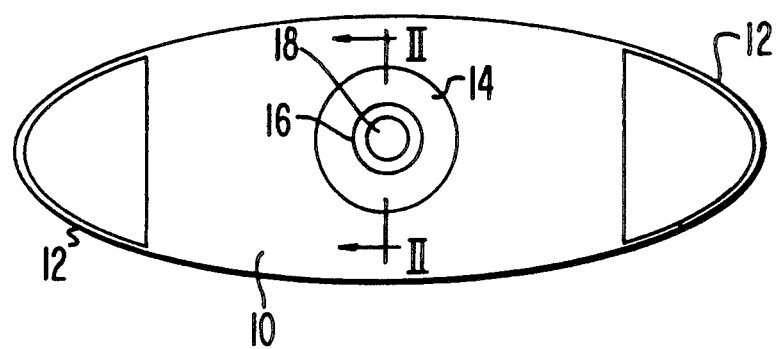
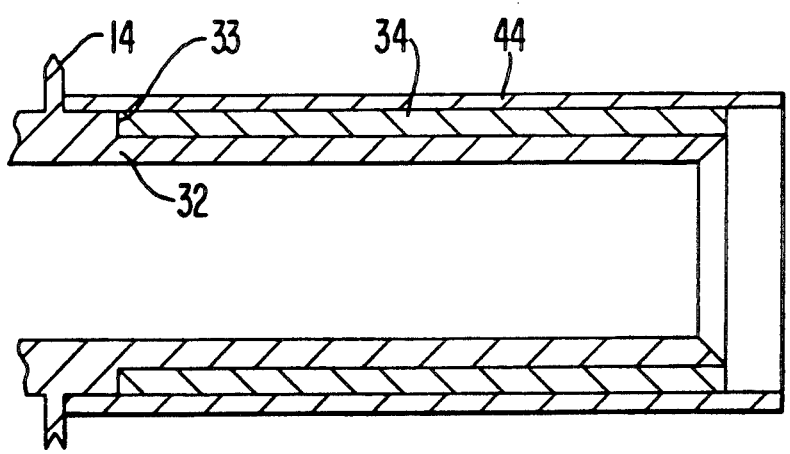

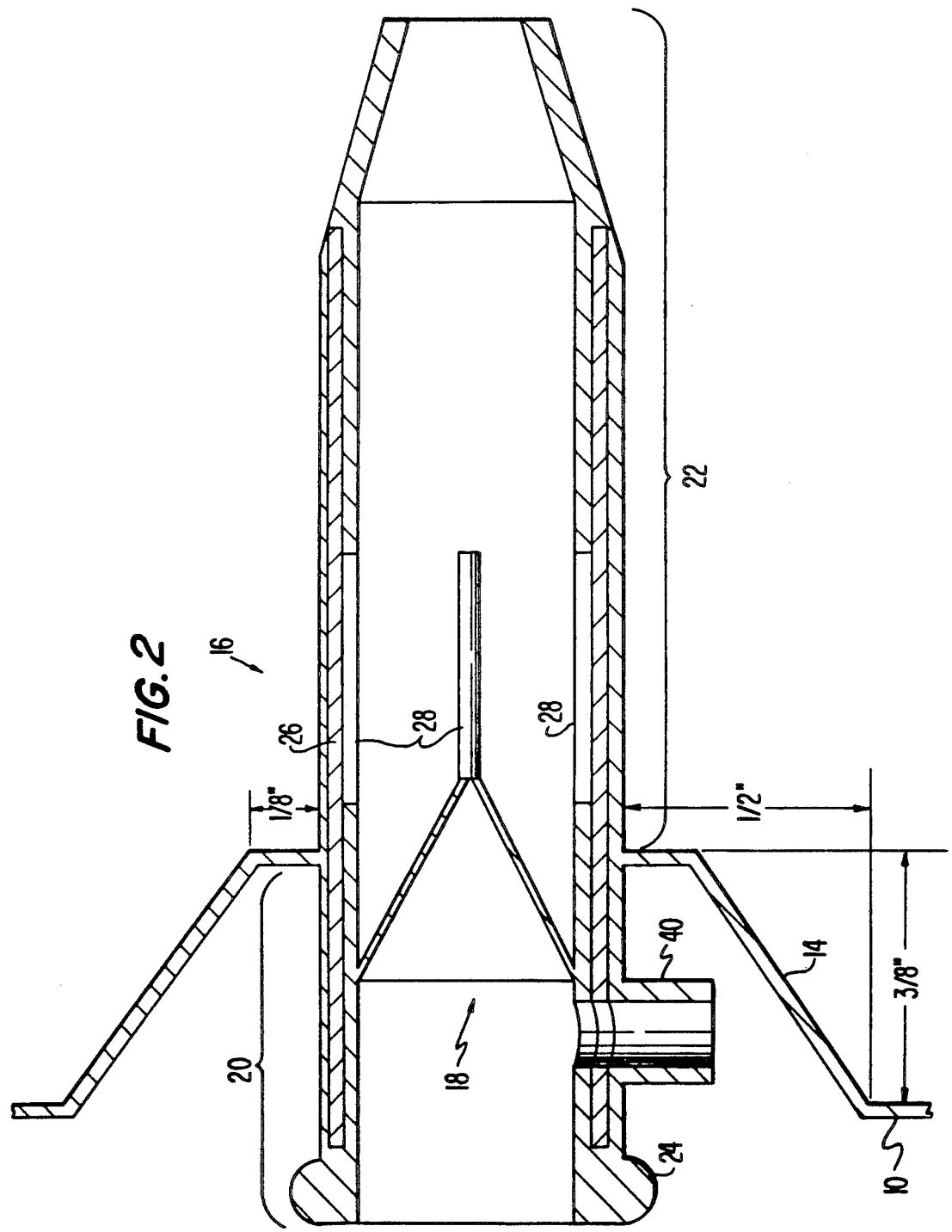

RESUSCITATION AID

CROSS REFERENCE TO RELATED APPLICATION

This is a continuation-in-part of my copending application Ser. No. 07/419,658, filed on Oct. 11, 1989, now U.S. Pat. No. 4,998,530 entitled RESUSCITATION AID and itself a continuation-in-part of my application Ser. No. 07/202,101, filed on June 1, 1988, entitled MASK FOR PERFORMING RESUSCITATION and now abandoned.

BACKGROUND OF THE INVENTION

The present invention relates to an improvement in resuscitation aids, particularly devices for facilitating mouth-to-mouth resuscitation, of the type described in application Ser. No. 07/419,658.

As used herein, mouth-to-mouth resuscitation refers to methods in which air is forced from the lungs of a rescuer into the lungs of a victim of stopped breathing at regular intervals to provide the interchange of air necessary for respiration. If a victim of stopped breathing is to be saved from death, resuscitation must be started promptly after the cessation of breathing. At times, the heart may also have stopped, in which case simultaneous cardiac resuscitation will also be necessary.

Mouth-to-mouth resuscitation, frequently referred to as the "kiss of life", is a technique which is known to a significant portion of the population, particularly since it is not difficult to learn and does not require special equipment.

Unfortunately, the classic mouth-to-mouth technique requires direct contact between rescuer and victim, and many individuals find this aspect of the technique objectionable. Such objections have become even more prevalent because of the fear of transmission of the AIDS virus, given that a victim is often a stranger to a potential rescuer. Because of this fear, even trained paramedic personnel have become reluctant to administer mouth-to-mouth resuscitation.

Many devices have been developed for performing resuscitation in which no mouth-to-mouth contact is required between rescuer and victim. These devices usually involve inserting some type of tube into the airway of a victim. Among these devices are intubation devices, esophageal obturator airways and "bag valve mask" devices.

In order for such devices to be fully effective, they should establish an effective seal over the victim's mouth when air is being breathed into the victim. Many of the known devices are incapable of forming such a seal.

In addition, many known devices are relatively complicated and expensive so that they could not be made widely available for general use. Since resuscitation must be started within minutes after a stoppage of breathing, devices which cannot be made widely available and/or which can only be used by a small number of highly trained personnel are of little practical value.

Thus, mouth-to-mouth resuscitation remains the technique which offers the greatest hope of assistance to a victim of stopped breathing. Because the lips and associated facial muscles of such a victim are flaccid, virtually no known resuscitation aid can produce a perfect seal with the victim's lips. A nearly perfect seal can be created, however, if the rescuer purses his lips and then covers the victim's mouth. Such perfect seal is due in large measure to the ability of the rescuer to close his lips over the mouth area of the victim and thus perfectly conform to that area.

Pending U.S. application Ser. No. 202,101, filed on June 1, 1988, describes a disposable device which enables such a seal to be created while preventing the transmission of air and other fluids from the victim to the rescuer.

The invention disclosed in application Ser. No. 07/419,658 resolves many of these problems by providing a device which includes: a sheet of a flexible material forming a barrier to micro-organisms, the sheet being dimensioned to completely cover the victim's mouth, the sheet having an opening and a shaped portion which surrounds the opening and is shaped to allow the rescuer's lips to form an air-tight seal with the victim's lips when the rescuer is blowing air into the victim's mouth, the sheet, including the shaped portion, being formed to permit the victim to exhale without obstruction when the rescuer's lips are withdrawn from the sheet; a tubular member defining a confined air passage extending through the opening and having a first portion located to be inserted into the victim's mouth and over the victim's tongue when the sheet is in place and a second portion located to be inserted into the mouth of the rescuer; and means defining a one-way valve fastened to the tubular member for permitting free passage of air only from the rescuer to the victim.

SUMMARY OF THE INVENTION

It is a primary object of the present invention to improve the above-described mask.

A more specific object of the invention is to provide an improved mask which offers a greater degree of protection against transmission of disease-causing viruses and bacteria from the victim to the rescuer.

The above and other objects are achieved, according to the present invention, in a medical device for enabling a rescuer to administer mouth-to-mouth resuscitation to a victim while maintaining a sanitary barrier between victim and rescuer, which device includes:

a sheet of a flexible material forming a barrier to micro-organisms, the sheet being dimensioned to completely cover the victim's mouth, the sheet having an opening and a shaped portion which surrounds the opening and is shaped to allow the rescuer's lips to form an air-tight seal with the victim's lips when the rescuer is blowing air into the victim's mouth, the sheet, including the shaped portion, being formed to permit the victim to exhale without obstruction when the rescuer's lips are withdrawn from the sheet;

a tubular member defining a confined air passage extending through the opening and having a first portion located to be inserted into the mouth of the rescuer and a second portion located to be inserted into the victim's mouth and over the victim's tongue when the sheet is in place; and means defining a one-way valve fastened to the tubular member for permitting free passage of air only from the rescuer to the victim, by the improvement wherein the valve is supported by the first portion of the tubular member.

As of the filing date of copending application Ser. No. 07/419,658, the precise location of the one-way valve in the tubular member was not considered to be of particular importance and a location in the second portion of the tubular member was selected, partly because it was thought that this might facilitate manufacture of a one-piece mask.

However, further consideration reveals that if the one-way valve is in the second portion of the tubular member, then even if that portion of the tubular member includes a relatively rigid tube that will prevent the victim from involuntarily closing the airway, even slight deformations of the second portion of the tubular member by involuntary biting movements on the part of the victim can result in a slight opening of the valve when air is not being expelled by the rescuer. Since viruses can pass through even the smallest opening, the safety afforded by this mask could be compromised.

When, according to the present invention, the one-way valve is relocated to the first portion of the tubular member, which is to be located in the rescuer's mouth, this potential problem is avoided. The rescuer, being conscious, has a greater degree of control over the movements of his mouth than does an unconscious victim and the normal mouth movements associated with mouth-to-mouth rescucitation include no more than gentle biting action on the part of the rescuer.

BRIEF DESCRIPTION OF THE DRAWING

FIG. 1 is an elevational view of a preferred embodiment of a mask according to the present invention.

FIG. 2 is a cross-sectional view of the airway portion of the mask of FIG. 1, taken along the line II—II of FIG. 1.

FIG. 3 is a view similar to that of FIG. 2 of a second embodiment of an airway according to the present invention.

DESCRIPTION OF THE PREFERRED EMBODIMENTS

Figure 4:
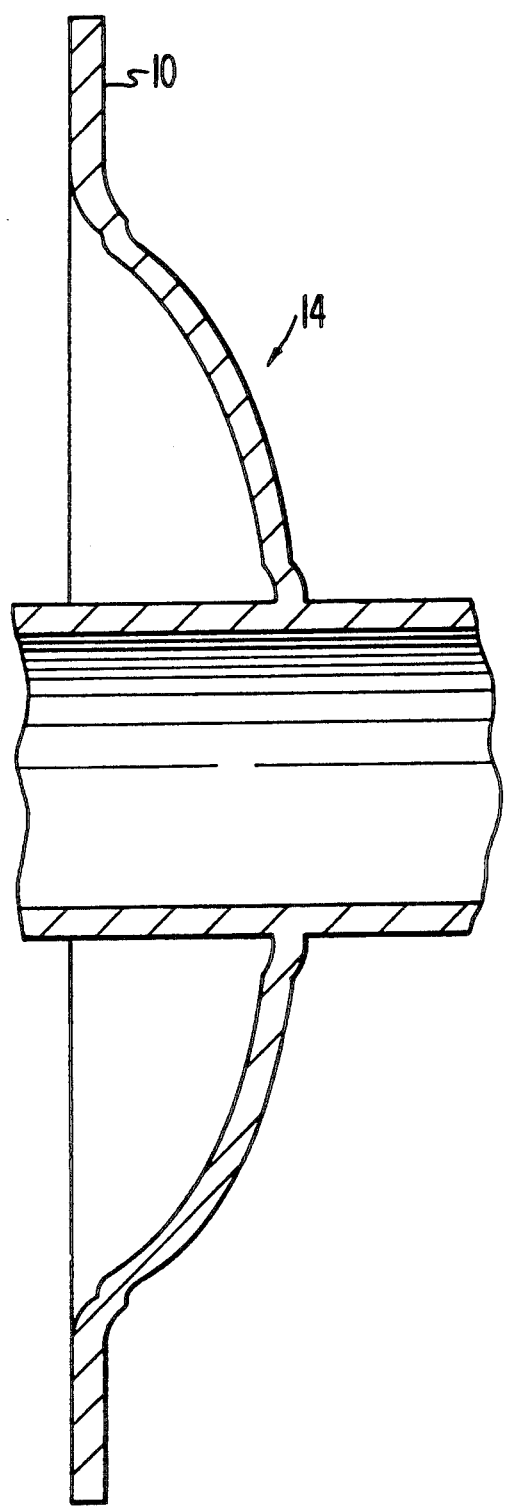
FIG. 4 is a detail view illustrating the shape assumed by a portion of the mask of FIGS. 1 and 2 when the mask is in use.

The mask shown in FIGS. 1 and 2 is essentially a one-piece molded plastic article preferably made of a flexible, transparent or semi-transparent plastic or a clear silicone rubber, the latter material presently being preferred. As shown in FIG. 1, the mask is composed of a generally elliptical cover sheet 10 provided at its ends with straps 12 which are preferably molded integrally with sheet 10. Essentially at the center of sheet 10 there is provided a frustoconical lip portion 14 which is connected to a tube 16 provided with a one-way valve 18 and constituting an airway via which air can be transferred from the rescuer to the victim. In addition, the mask is sized to cover the victim's nostrils. Even though the mask covers the victim's nostrils, it is still necessary for the rescuer to pinch the victim's nose when exhaling into the victim, in accordance with standard CPR practice. However, if the victim's nostrils are covered by the mask, the mask will serve as a barrier protecting the rescuer from contamination in the event the victim experiences vomiting through the nose during resuscitation.

As shown in FIG. 2, tube 16 and its associated valve 18 are preferably molded integrally with sheet 10 and lip portion 14.

According to one advantageous feature of the present invention, the mask is to be secured in place on the victim, with straps 12 placed around the victim's ears, rather than being worn by the rescuer. Therefore, once tube 16 has been inserted into the victim's mouth and properly positioned, it will remain in place even if the rescuer should remove his mouth from tube 16.

Referring now more specifically to FIG. 2, tube 16 includes a first portion 20 located at the side of the mask which will face the rescuer and a second portion 22 which will be inserted into the victim's mouth at the time the mask is placed on the victim. According to the invention, valve 18 is supported by portion 20. A bead 24 around the free end of portion 20 assists retention of portion 20 in the rescuer's mouth. Portion 22 is given a length sufficient to assure that it will rest upon the victim's tongue without extending so far as to contact the victim's throat, which would cause gagging, and possible vomiting. It is presently contemplated that this will be achieved if portion 22 has a length of the order of 2 to 2¼ inches. Preferably, portion 20 has a length of the order of ¾ to 1 inch.

Lip portion 14 constitutes a significant component of the mask in that its configuration assures that the rescuer's lips can use lip portion 14 to form a "kiss" which creates an air-tight seal with the victim's lips during the times when the rescuer is blowing air into the victim's mouth, even though the victim's lips are usually flaccid. In effect, the form of lip portion 14 has been painstakingly developed to allow the rescuer's lips to establish an effective seal which makes possible efficient delivery of air to the victim's lungs to an extent comparable to that which can be achieved by direct contact mouth-to-mouth resuscitation.

Moreover, the function of lip portion 14 is such that when the rescuer's mouth is withdrawn, the victim can readily exhale around portion 14.

The preferred relevant dimensions for lip portion 14 are shown in FIG. 2 for a mask made of 50 Durometer clear silicone rubber with lip portion 14 having a thickness of the order of 1/16 inch. The dimensions shown in FIG. 2 have been found to be suitable for individuals having a wide range of sizes. Bead 24 can assist the rescuer to place his mouth in the correct position relative to lip portion 14

As can be seen from both FIGS. 1 and 2, valve 18 is preferably of the type having two flat sides which meet at a closing line, the valve thus being of the type which is referred to a "fish mouth" valve. When a valve of this configuration is made of the type of material described above, one effective example being as described above (50 Durometer clear silicone rubber, with a wall thickness of the order of 1/16 inch), it has been found that this valve will open easily to permit the passage of air in the direction from the rescuer to the victim, but will form a tight seal with respect to the transmission of air in the opposite direction. In fact, tests have shown that this valve is impermeable to the transmission of the AIDS virus in the direction from the victim to the rescuer.

At the free end of portion 22, tube 16 extends a sufficient distance to provide a protective enclosure which will reduce the possibility that the victim's tongue can assume a position to block the airway provided by tube 16.

Embedded within portions 20 and 22 of tubular member 16 is a tube 26 which is relatively rigid, and which may be constituted, for example, by an acrylic or polycarbonate plastic having a thickness of the order of 1/16 inch. The part of tube 26 which is located in portion 20 serves to prevent the rescuer from deforming valve 18, while the part of tube 26 which is located in portion 22 will be interposed between the teeth of a victim when the mask is in place and thus serves to prevent the victim from involuntarily closing the airway or biting through tube 16.

Tube 26 may be molded in place in the molded silicone rubber mask by being placed on a core having four radial projections which support the inner surface of tube 26, silicone rubber then being molded around tube 26 as the mask is being produced. When the resulting mask is removed from the mold, the radial projections of the core will leave slots 28, as shown in FIG. 2. Between slots 28, silicone rubber adheres to the inner surface of tube 26.

According to a particularly advantageous embodiment of the tube 16 shown in FIG. 2, this tube has an interior diameter of the order of 0.6 to 0.7 inch and a wall thickness of the order of 0.04 to 0.1 inch, although other dimensions may prove suitable.

Generally, tube 16 has a circular cross section and it is particularly preferred that at least portion 20 have this cross section so that the rescuer can grip portion 20 in his mouth with his head having any orientation relative to that of the victim.

A second embodiment of a tube according to the present invention is illustrated in FIG. 3. This tube is structurally simpler than that of FIG. 2 and is composed of a molded body 32 of soft rubber. Valve 18 has the same location as in FIG. 2 and does not appear in FIG. 3. Tube 32 is additionally provided, in the vicinity of lip portion 14, with an annular shoulder 33 and carries a rigid plastic tube 34 which is positioned against shoulder 33. Tube 34 may be made of the same material as tube 26 of FIG. 2 and performs essentially the same function. An embodiment employing the tube shown in FIG. 3 is otherwise identical to that shown in FIG. 2 and includes, in particular, a portion (not shown) which is to fit into the rescuer's mouth.

As noted earlier herein, the device is placed into use by inserting portion 22 into the victim's mouth so that the distal end of tube 16 or 32 lies upon the victim's tongue.

If, during a resuscitation procedure, the victim should experience vomiting, this can be dealt with by removing one of the straps 12 and pulling tube 16 out of the victim's mouth. Since the other strap 12 remains in position, the mask can be easily reinserted after the vomiting episode has terminated.

One feature of a mask according to the present invention is that it does not include any parts which obturate the victim's nose or which must be fit over the victim's chin, so that installation of the mask is simplified.

Embodiments of the invention could also be constructed to include an opening for connection of an auxiliary air supply device and/or to include electrodes via which impulses could be supplied to the victim's tongue and/or lips to perform a cardiac pacing or defibrillation function.

Thus, as shown in FIG. 2, tube portion 20 may be optionally provided with a nipple 40 for connection to an auxiliary air or oxygen supply.

As shown in FIG. 3, the mask may be packaged with a cylindrical metal electrode 44 connected to a wire for use, together with a second electrode, to effect defibrillation, or cardiac pacing. Electrode 44 may be open or closed at its distal end and can be used while mounted on tube 34 or by itself. When electrode 44 is open at its distal end, as shown in FIG. 3, and is installed on tube 34, defibrillation or pacing can be performed simultaneously with resuscitation. The other electrode may be connected to any suitable location on the victim's body.

Referring now to FIG. 4, there is shown the configuration assumed by lip portion 14 when the mask is positioned to perform a resuscitation procedure. At this time, sheet 10 rests against the victim's face so that lip portion 14 flexes. Sheet 10 is formed, by molding, so that the inner and outer peripheries of lip portion 14 form sharply defined angles with adjacent parts of sheet 10. As a result, when sheet 10 rests against the victim's face, lip portion 14 takes on a bowed, or arcuate, shape which is concave toward the victim's mouth and tends to encompass the victim's lips.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In a medical device for enabling a rescuer to administer mouth-to-mouth resuscitation to a victim while maintaining a sanitary barrier between victim and rescuer, which device includes:

a sheet of a flexible material forming a barrier to micro-organisms, said sheet being dimensioned to completely cover the victim's mouth, said sheet having an opening and a shaped portion of circular form which surrounds said opening and is shaped to allow the rescuer's lips to form an air-tight seal with the victim's lips when the rescuer is blowing air into the victim's mouth, said sheet, including said shaped portion, being formed to permit the victim to exhale without obstruction when the rescuer's lips are withdrawn from said sheet;

a tubular member defining a confined air passage extending through said opening and having a first portion located to be inserted into the mouth of the rescuer and a second portion located to be inserted into the victim's mouth and over the victim's tongue when said sheet is in place; and means defining a one-way valve fastened to said tubular member for permitting free passage of air only from the rescuer to the victim, the improvement wherein said valve is supported by said first portion of said tubular member.

2. A device as defined in claim 1 wherein said sheet, said tubular member and said valve are constituted by a one-piece molded member.

3. A device as defined in claim 2 wherein said molded member is of a silicone rubber.

4. A device as defined in claim 3 wherein said silicone rubber is a 50 Durometer silicone rubber.

5. A device as defined in claim 1 further comprising a second tubular member of a rigid material held in place relative to said first-recited tubular member to surround the air passage and extending along both said first portion and said second portion of said first-recited tubular member, said second tubular member serving as a bite block to prevent the victim from closing the air passage and to prevent the rescuer from deforming said valve.

* * * * *

UNITED STATES PATENT AND TRADEMARK OFFICE
CERTIFICATE OF CORRECTION

PATENT NO.   :   5,095,898
DATED        :   March 17, 1992
INVENTOR(S)  :   T. Anthony Don Michael It is certified that error appears in the above-indentified patent and that said Letters Patent is hereby corrected as shown below:

On the Title page, item [75], correct the spelling of the inventor's middle name to be:

--Anthony--.

Signed and Sealed this

Eighth Day of June, 1993

Attest:

MICHAEL K. KIRK

*Attesting Officer*    Acting Commissioner of Patents and Trademarks